United States Patent [19]

Prohaska

[11] Patent Number: 5,116,495
[45] Date of Patent: May 26, 1992

[54] CAPILLARY CHROMATOGRAPHY DEVICE

[75] Inventor: Otto J. Prohaska, Cleveland Heights, Ohio

[73] Assignee: OttoSensors Corporation, Cleveland, Ohio

[21] Appl. No.: 455,502

[22] Filed: Dec. 22, 1989

Related U.S. Application Data

[63] Continuation of Ser. No. 96,137, Sep. 11, 1987, abandoned.

[51] Int. Cl.$^5$ .............................................. B01D 15/08
[52] U.S. Cl. ................................. 210/198.2; 210/656; 210/658; 210/198.3; 55/386; 73/61.52; 422/70
[58] Field of Search ............... 73/61.1 C, 866, 864.83, 73/864.84; 210/658, 656, 198.2, 198.3; 422/70, 68.1, 82.01, 82.03; 55/386

[56] References Cited

U.S. PATENT DOCUMENTS

| | | | |
|---|---|---|---|
| 3,513,092 | 5/1970 | Matherne | 210/198.3 |
| 3,538,744 | 11/1970 | Karasek | 55/386 |
| 4,116,836 | 9/1978 | De Angelis | 55/386 |
| 4,348,286 | 9/1982 | Felton | 210/658 |
| 4,424,127 | 1/1984 | Roeraade | 55/386 |
| 4,591,524 | 5/1986 | Tyihak | 210/658 |
| 4,657,742 | 4/1987 | Beaver | 55/386 |
| 4,726,822 | 2/1988 | Cates | 55/386 |

FOREIGN PATENT DOCUMENTS 60-230058  11/1985  Japan ................................ 210/198.2

OTHER PUBLICATIONS

Patent and Trademark Office Translation of Japan Kokai No-60-230058, PTO-4179, Aug. 1990, pp. 1-10.
Snyder, Introduction to Modern Liquid Chromatography, John Wiley & Sons Inc., New York (1979) pp. 125, 126, 227, 519-522 and 625.
A Gas Chromatographic Air Analyzer Fabricated on a Silicon Wafer, Terry, IEEE Transactions of Electronic Devices vol. ED-26, No. 12, Dec. 1979 pp. 1880-1886.
The Wall-Jet Electrochemical Detector in Normal HPLC Gunasingham et al.; Analytical Chemistry Symposia Series, vol. 17, Chemical Sensors 1983 pp. 561-565.
Acetylcholine and Choline in Neuronal Tissue Measured by HPLC with Electrochemical Detection; P. E. Potter, J. Neurochem vol. 41 No. 1, 1983, pp. 188-194.
Capillary Liquid Chromatography in Field Flow Fractionation-Type Channels; J. C. Gidding; J. Chromatography 255 (1983) pp. 359-379.
Liquid Chromatography in Open-Tubular Columns; Jorgenson, J. Chromatography, 255 (1983) pp. 335-348.
Theoretical Aspects of LS with Packed and Open Small-Bore Columns; Knox, J. Chromatography Science, vol. 18, Sep. 1980 pp. 453-461.

Primary Examiner—Ernest G. Therkorn
Attorney, Agent, or Firm—Calfee Halter & Griswold

[57] ABSTRACT

The invention describes a new fabrication procedure of a capillary chromatography device with at least one sensor unit. The device contains at least one capillary column which is formed between a carrier and a cover layer, and which has at least one inlet and one outlet opening for a carrier phase and/or the sample. In addition, the invention describes a capillary chromatography device with at least one sensor, where the capillary columns with inlet and outlet openings and, if necessary, additional inlet, outlet and detector chambers, are formed between a carrier and a cover layer, which is deposited onto the carrier surface.

16 Claims, 2 Drawing Sheets

CAPILLARY CHROMATOGRAPHY DEVICE

This is a continuation of Ser. No. 096,137, filed Sep. 11, 1987 now abandoned.

The aim of the invention, is to describe a process which allows the fabrication of even complexly designed capillary chromatography devices in a simple manner and in high quantities. This process can be achieved in that removeable, i.e., dissolvable, substance, i.e. photoresist, is applied with the shape of the capillary columns, with widths of less than 1 $\mu$m and up to 1 mm, heights of up to 1 mm preferably 0.5 $\mu$m to 3 $\mu$m, as well as the shape of possible additional inlet, outlet and detector chambers and in that the removable substance as well as the carrier is covered by a cover layer of at least 0.5 $\mu$m, preferably 3 $\mu$m thickness, which is formed either by evaporation, and/or sputtering and/or plasma enhanced chemical vapor deposition (PECVD) methods or by spinning, dropping, dipping, or electrolytic methods. Afterwards, the removeable substance is dissolved through the inlet and/or outlet openings and the resulting cavities between the substrate and the cover layer are forming the capillary columns, the inlet, the outlet and the detector chambers for the carrier phase and/or the sample. The essential advantage of this invented process is that there is no etching procedure necessary to form the columns whereas the device configuration can be achieved by deposition of one or several out of a series of specific cover layers on almost any substrate or carrier layer. The device has new applications since the substrate and the cover layer can be at least a magnitude smaller than the devices formed by known procedures. In addition, complicated structure designs can be achieved which cannot be obtained by using conventional methods, such as etching or mechanical treatment. It is advantageous to form indentations in the carrier or carrier layer, i.e. by etching, before the deposition of the removeable substance in order to increase the cross section of the capillary column.

The invented capillary chromatography device is characterized in that the surface of the substrate or carrier layer as well as a removeable substance, which is deposited onto the substrate or the carrier layer and which has the shape of the inside of the capillary columns, inlet, outlet, and dectector chambers, and which was evaporated, sputtered, using PECVD or electrolytical methods, or spun on, dipped in or dropped on, consisting i.e. of photo resist, is covered by a covered layer consisting of $SiO_x$, $SiO_x$, $N_y$, $TiO_x$, $Ta_yO_y$, where x varies between 1 and 2 and y varies between 1 and 5, or consisting of other inorganic or organic substances, such as polymers or other substances with similar mechanical or electrical qualities and which forms the capillary columns, the inlet, outlet and detector chambers together with a substrate when the removeable substance is removed. The wall thickness of the cover layer is at least 0.5 $\mu$m, preferably 3 $\mu$m. The inside of the columns and chambers can be covered with polar or unpolar layers in order to improve substance separation. The capillary columns are preferably of rectangular cross section with a height between less than one micrometer and more than 1 mm, preferably 3 $\mu$m, the widths between less than 1 $\mu$m and more than 1 mm. The sensors can be formed by electrochemical or physical sensors, UV, florescense, refraction detectors, spectrometers, etc.

A product is achieved by the invented fabrication method which can be made very precisely since it is very easy to cover the inside walls of the capillary chromatography columns with evaporated or chemically deposited separation enhancing layers. The fabrication process allows the design of almost any shape desired for optimised performance of columns and chambers, which can split up or combine, etc., a design which is hardly or not at all achievable by presently known etching techniques.

These capillary chromatography devices are especially useful for liquid chromatography measurements. The detector system at the end of the column can be preferably designed as an electrochemical cell which can be integrated into the system by a chamber type design so that the carrier phase and the sample can be finally disposed through an outlet opening. Another possibility of the invented design is that the sensors are arranged within the capillary columns, improving recording procedures. Depending on the application, it can be advantageous to form the columns meander, spiral, double helix or bifilar like, and/or change the cross section of the columns along its continously and/or discontinously. It also can be advantageous to design the capillary column of a group of columns, arranged to be parallel, next to and/or above each other, and/or to split up into a multitude of columns and/or is combine out of a multitude of columns, and/or to allow connections among the columns in order to improve the mixture and/or separation between carrier phase and sample and sample components. Otherwise thus very small capillary chromatography devices can be arranged within the very small area and designed especially for very specific measurements with that invented fabrication procedure whereas otherwise long capillary columns or sets of columns would have to be made in the conventional way.

It is also space reducing as soon as two detector systems are arranged in series connection or two capillary chromatography units are integrated onto one substrate or as soon as at least two integrated capillary chromatography devices are connected in series.

The invention also permits the fabrication of columns which can be supplied through at least two different inlet openings, or chambers can be combined, or various columns leading to at least two detector systems, can be supplied through one inlet opening or chamber, where an inlet or outlet opening is directly etched into the column or it's chamber-type establishment.

The special advantages of the invented capillary chromatography devices and its fabrication process is not only that it can be inexpensively reproduced in a compact, reproducible form by means of thin-film technology equipment, but that also well defines capillary columns of micrometer or submicrometer sectional dimensions can be achieved and reproduced with high precision, in contrary to commonly used procedures (see J. C. Giddings, G. P. Chang, M. N. Myers, J. M. Davis, K. D. Coldwell: Capillary liquid chromatography in field flows fraction-action-type channels. J. Chromatography, 225, 359–379, 1983). Theoretical considerations showed that capillary columns of cross sectional dimmensions in the range of micrometers achieve extremely high separation qualities at very short retention times (see J. H. Knox: Theoretical Aspects of LC with packed and open small-hole columns. J. Chromotographic Sciences, 18, 453–463, 1980; and J. W. Jorgenson, E. J. Guthrie: Liquid chromatography in open-tubular columns. J. Chromatography, 255, 335-348, 1983). The invented devices therefore represent high resolution, time saving instruments.

An essential additional advantage over known devices is that the columns, the splitting systems as well as the detector units can be formed between the substrate and the cover layer which is partially bent upwards, it forms the columns and chambers, since the cover layers adhere strongly to the substrate and form a strong seal and at the same time enable the establishment of the column-chamber system in one fabrication step, as soon as the removeable substance is defined with respect to the detector system and the detector connections as well as the possible inlet and outlet orifices through the substrate.

Additional advantages are in that the columns inside walls can be covered by various layers, i.e. aluminum oxide, carbon, etc., in order to increase the separation efficiency and in that the length and cross sectional dimensions can be varied in very defined manners, columns can be combined and split up, inlet and outlet chambers can be added and devices can be combined in an on-chip integrated way, achieving certain, well defined measurement qualities.

DESCRIPTION OF THE PREFERRED EMBODIMENTS

Figure 1A:
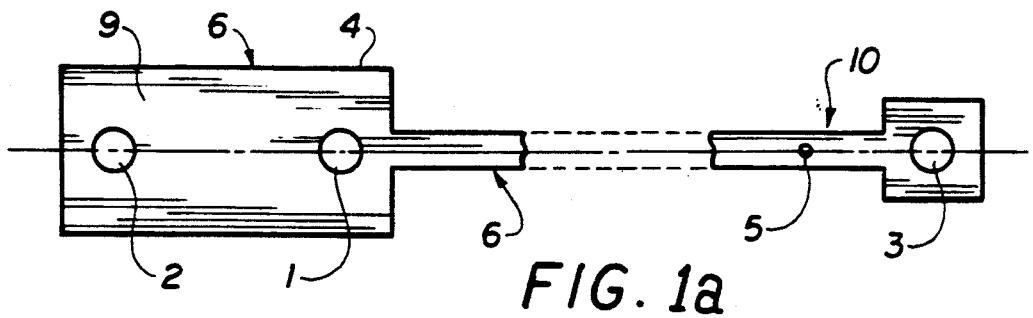
FIG. 1a shows the top view of a capillary chromotography device and FIG. 1b a cross section of the device.
Figure 1B:
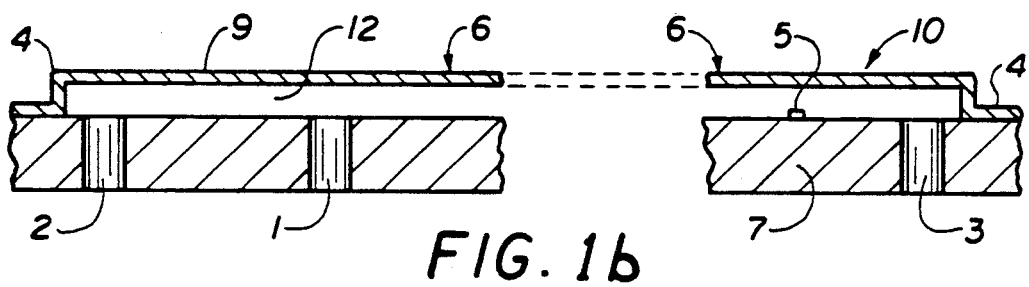

In FIGS. 1a and b is shown that the cover layer (4) is bent upwards with respect to a substrate (7) in such a way that at least one capillary column (6) is formed between the cover layer (4) and the substrate (7). The cover layer (4) forms together with the substrate (7) also a splitting system (9) with the result that the carrier phase and/or the sample (12) can enter through an inlet opening, which is placed in this case through the substrate (7), and in part can go through the capillary column (6) and in part can go through the output opening (2), which in this case is placed through the substrate (7). The splitting-system is advantageous for the quantification of the very small sample volume in the range of nanoliters. The cover layer (4) also can form a detector unit (10) together with the substrate (7) in defining measurement chambers which contain the sensors (5). the carrier phase as well as the sample (12) penetrates through the outlet orifice (3), which in this case is formed by a hole through the substrate.

Technological fabrication procedures and materials are used for the invented capillary chromatography devices which are similar to the ones which had been developed for integrated circuits, or thin-film probes, however, different process parameters are required in some cases in order to obstain certain layer qualities. Thin-film sensors are integrated, if appropriate; in the detector system (10) forming i.e. electrochemical sensors (5), improving and simplifying the measurements. The splitting-system (9) is also formed, when appropriate, by the cover layer (4) and the substrate (7), at the same time as the capillary columns (6) and the detector systems (10) are formed. The splitting-systems improves and simplifies the column filling process since the sample (12) enters through the inlet orifice (1) and proceeds through the capillary column (6) to the sensors (5), exiting through the outlet opening (3) and the sample (12) also moves through the wider splitting-channel (9') exiting through the outlet orifice (2), without exiting capillary column (6) or the detector system (10).

Figure 2A:
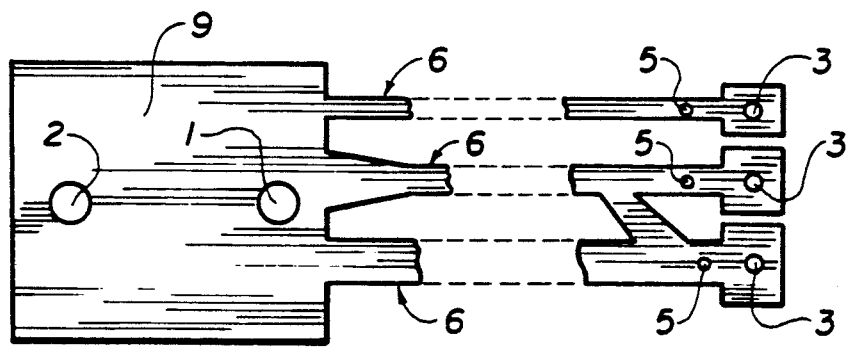
FIG. 2a shows a capillary column composed of a set of small columns and FIG. 2b a cross section of such a column set.
Figure 2B:
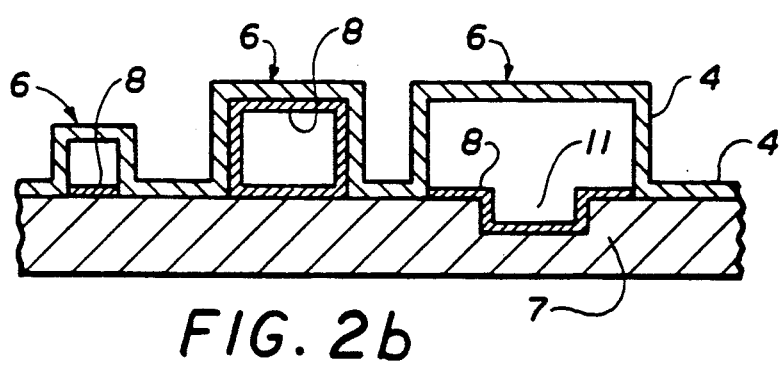
Figure 3A:
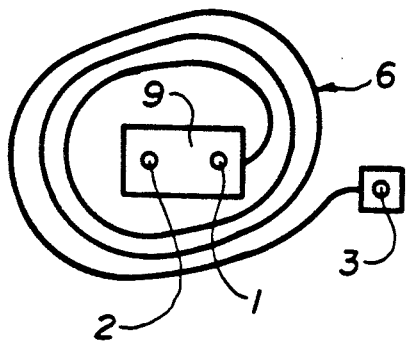
FIGS. 3, a, b, c and d shows various possible capillary column device designs.
Figure 3B:
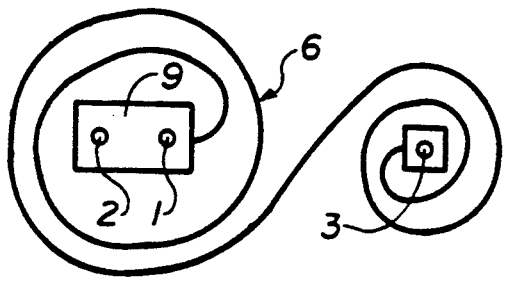
Figure 3C:
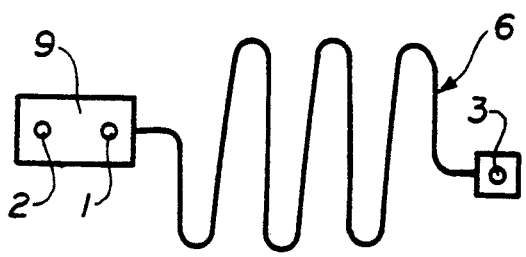
Figure 3D:
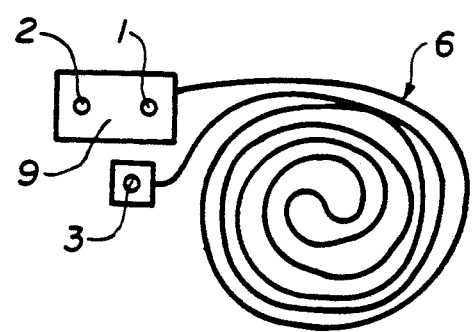

FIG. 2b shows a rectangular cross section of the capillary columns (6), which is formed in that the cover layer (4) which is deposited onto the substrate (7) is bent upwards. In order to increase the separation qualities of the capillary columns (6) they can be modified inside by polar or unpolar layers (8). Engraved identations, that is the capillary columns (6) enlarging groves (11), which i.e. are etched into the substrate (7) can increase the cross sectional area of the capillary columns (6); the cross sectional dimensions may range from submicrometer values up to millimeter values.

The capillary column (6) can be designed in the shape of a meander, spiral, double helix or bifilar on top of the substrate (7). Examples are shown in FIG. 3 a, b, c, and d. The cross section of the capillary columns (6) can be kept constant over the total length of the column or can be changed continously or abruptly. FIG. 2a shows that the capillary column (6) can also be designed as a column system which can show columns running in parallel and/or single columns splitting up and/or converging of several columns to one column and/or interconnections among the columns in order to obtain additional mixture or separation effects.

Figure 4:
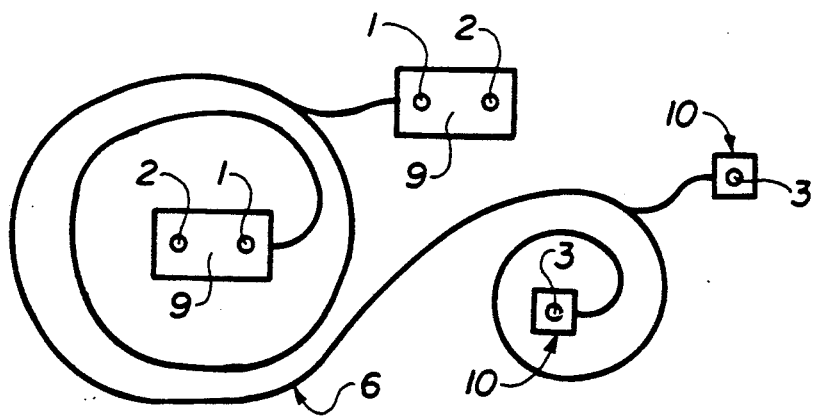
FIG. 4 shows a possible combination of several capillary column devices.

A combination of several capillary chromatography units, preferably by integration on one insulating substrate (7), is shown in FIG. 4, as an example where the capillary column (6) is supplied through several splitting systems (9) and ends in various detector systems (10). This, for instance, enables the possibility to add carrier phases and/or samples (12) at arbitrary times and at arbitrary locations in a capillary column (6) and broadens the application range of the integrated capillary chromatography device.

I claim:

1. A capillary chromatography device for separating the components of a sample, said device comprising:
   means defining a capillary column for conducting the sample therethrough, the cross-section of said capillary column having a width less than or equal to 1 millimeter and a height less than or equal to 1 millimeter;
   at least one inlet and at least one outlet for conducting the sample into and out of said capillary column;
   at least one sensor located in said capillary column for measuring a characteristic of the sample;
   said means defining a capillary column including first and second walls, said first wall comprising a substrate and said second wall comprising a cover layer having opposite portions sealingly adhered to a surface of said substrate and partially upwardly bent portions therebetween, said cover layer having a thickness in the range of 0.50 micrometers to 3 micrometers and being formed of a material selected from the group of materials consisting of $SiO_x$, $SiO_xN_y$, $SiN_y$, $TiO_x$, and $TaO_x$, and $TaO_y$, and where x can vary between 1 and 2 and where y can vary between 1 and 5.

2. A capillary chromatography device as set forth in claim 1 wherein said substrate includes at least one groove etched therein for increasing the cross section of said capillary column.

3. A capillary device as set forth in claim 2 wherein the cross-sectional area of said groove is substantially less than the cross-sectional area of said capillary column.

4. A capillary chromatography device as set forth in claim 1 wherein said capillary column includes on its inner surface a separation enhancing layer.

5. A capillary device as set forth in claim 1 wherein said sensor is located between said inlet and said outlet.

6. A capillary device as set forth in claim 1 wherein said substrate and said cover layer together define a splitting system which includes an output opening whereby said sample may enter the capillary column through said inlet and a portion of said sample may travel through the capillary column and the remaining portion may travel through said output opening.

7. A capillary device as set forth in claim 1 wherein said cover layer determines the inner shape of said capillary column.

8. A capillary device as set forth in claim 1 wherein the height of said bent cover portions determines the height of said capillary channel.

9. A capillary device as set forth in claim 1 wherein said inlet and said outlet are formed by openings in the substrate.

10. A capillary chromatography device as set forth in claim 1 wherein said capillary column has the shape of a spiral.

11. A capillary chromatography device as set forth in claim 1 wherein said capillary column has the shape of a double helix.

12. A capillary chromatography device as set forth in claim 1 wherein said capillary column has a bifilar shape.

13. A capillary chromatography device as set forth in claim 1, 10, 11, or 12 wherein the cross-section of said capillary column changes continuously along the length of said capillary column.

14. A capillary chromatography device as set forth in claim 1, 10, 11, or 12 wherein the cross-section of said capillary column changes abruptly along the length of said capillary column.

15. A capillary chromatography device as set forth in claim 1 wherein said substrate and said cover layer define a plurality of capillary columns extending parallel to each other.

16. A capillary chromatography device as set forth in claim 1 wherein said substrate and said cover layer define a plurality of capillary columns extending in different directions and merging into each other.

* * * * *

UNITED STATES PATENT AND TRADEMARK OFFICE
CERTIFICATE OF CORRECTION

PATENT NO. : 5,116,495
DATED : May 26, 1992
INVENTOR(S) : Otto J. Prohaska

It is certified that error appears in the above-identified patent and that said Letters Patent is hereby corrected as shown below:

On title page, insert below the "Assignee"

--[*] Notice: The portion of the term of this patent subsequent to July 2, 2008 has been disclaimed.--

Signed and Sealed this

Sixteenth Day of November, 1993

Attest:

BRUCE LEHMAN

Attesting Officer

Commissioner of Patents and Trademarks